United States Patent
Onishi et al.

(10) Patent No.: US 9,610,583 B2
(45) Date of Patent: Apr. 4, 2017

(54) REAGENT BOTTLE WITH ASPIRATION PIPE

(71) Applicants: Beckman Coulter, Inc., Brea, CA (US); DHR Technologies Ireland Limited, Dublin (IE)

(72) Inventors: Hiroyuki Onishi, Shizuoka (JP); Masato Kayahara, Shizuoka (JP); Hiroshi Suzuki, Shizuoka (JP); Ryusuke Furuya, Shizuoka (JP); Naoki Mukaiyama, Shizuoka (JP); Michael Cooney, County Clare (IE); Marcus O'Neill, County Clare (IE); Sean O'Mahony, County Clare (IE)

(73) Assignees: Beckman Coulter, Inc., Brea, CA (US); DTIL Ireland Holdings Ltd., Dublin (IE)

(*) Notice: Subject to any disclaimer, the term of this patent is extended or adjusted under 35 U.S.C. 154(b) by 57 days.

(21) Appl. No.: 14/723,286

(22) Filed: May 27, 2015

(65) Prior Publication Data

US 2015/0343446 A1    Dec. 3, 2015

Related U.S. Application Data

(60) Provisional application No. 62/003,453, filed on May 27, 2014.

(51) Int. Cl.
*B01L 3/00* (2006.01)
*B29C 49/04* (2006.01)
(Continued)

(52) U.S. Cl.
CPC .............. *B01L 3/523* (2013.01); *B29C 49/04* (2013.01); *G01N 35/1002* (2013.01);
(Continued)

(58) Field of Classification Search
CPC ..... B01L 3/523; B29C 49/04; B29C 49/4273; G01N 35/1002
(Continued)

(56) References Cited

U.S. PATENT DOCUMENTS 5,102,631 A    4/1992    Jordan et al.
5,405,055 A    4/1995    Hester
(Continued)

FOREIGN PATENT DOCUMENTS

DE    3838278    *    1/1990
DE    3838278 C1    1/1990
(Continued)

OTHER PUBLICATIONS

International Search Report and Written Opinion mailed on Dec. 1, 2015 for International Application No. PCT/US2015/032703 filed on May 27, 2015.

*Primary Examiner* — Jill Warden
*Assistant Examiner* — Dwayne K Handy
(74) *Attorney, Agent, or Firm* — K&L Gates LLP; Louis C. Cullman; Brian J. Novak

(57) ABSTRACT

An embodiment of a reagent container includes a bottle with a pipe to reduce the effects of reagent sloshing. The bottle has an elongated base and an opposed cover connected by side walls and an end wall. A flat platform surrounded by a raised rim lies in the base opposite an opening in the cover. A ribbed pipe frictionally fits within the bottle opening and may attach to the anchor region leaving vent passages around the pipe. The pipe includes an aperture adjacent to the anchor region and oriented toward the end wall so that sloshed fluid has only a small effect on the level of reagent in the pipe during transfers. A modified blow molding (Continued)

process produces the anchor region by extending a pin a predetermined distance into a mold while the molded material is still plastic.

14 Claims, 7 Drawing Sheets

(51) Int. Cl.
| | |
|---|---|
| *G01N 35/10* | (2006.01) |
| *B29C 49/42* | (2006.01) |
| *B29K 105/00* | (2006.01) |
| *B29L 31/00* | (2006.01) |
| *B29C 49/20* | (2006.01) |
| *B29C 65/08* | (2006.01) |
| *B29C 65/48* | (2006.01) |
| *B29C 65/58* | (2006.01) |
| *B29C 65/02* | (2006.01) |
| *B29C 65/06* | (2006.01) |

(52) U.S. Cl.
CPC . *B01L 2200/026* (2013.01); *B01L 2200/0684* (2013.01); *B01L 2200/12* (2013.01); *B01L 2200/16* (2013.01); *B01L 2300/042* (2013.01); *B01L 2300/0809* (2013.01); *B01L 2300/0851* (2013.01); *B01L 2300/0858* (2013.01); *B29C 49/20* (2013.01); *B29C 49/4273* (2013.01); *B29C 65/02* (2013.01); *B29C 65/06* (2013.01); *B29C 65/08* (2013.01); *B29C 65/48* (2013.01); *B29C 65/4895* (2013.01); *B29C 65/58* (2013.01); *B29C 2049/2047* (2013.01); *B29K 2105/258* (2013.01); *B29L 2031/712* (2013.01); *Y10T 29/49828* (2015.01)

(58) Field of Classification Search
USPC .......................................................... 422/556
See application file for complete search history.

(56) References Cited

U.S. PATENT DOCUMENTS

| | | | | |
|---|---|---|---|---|
| 5,406,995 | A | * | 4/1995 | Gantzer .................... B01F 3/08 |
| | | | | 137/576 |
| 5,497,916 | A | | 3/1996 | Hester |
| 5,842,076 | A | | 11/1998 | Glover et al. |
| 5,980,834 | A | | 11/1999 | Bruno |
| 6,378,741 | B1 | | 4/2002 | Loertscher |
| 8,003,053 | B2 | * | 8/2011 | Senftner .................... B01L 3/08 |
| | | | | 206/730 |
| 8,083,056 | B1 | | 12/2011 | Wu |
| 8,153,086 | B2 | | 4/2012 | Senftner et al. |
| 8,206,648 | B2 | * | 6/2012 | Sattler ..................... B01L 3/508 |
| | | | | 210/120 |
| 2011/0293478 | A1 | | 12/2011 | Robert et al. |
| 2013/0026124 | A1 | | 1/2013 | Wu |

FOREIGN PATENT DOCUMENTS

| | | | |
|---|---|---|---|
| EP | 189750 | A2 | 8/1986 |
| JP | 2007-047001 | A | 2/2007 |
| WO | 97/12677 | | 4/1997 |
| WO | WO 9712677 | * | 4/1997 |
| WO | 2004/028910 | A1 | 4/2004 |
| WO | 2009/086864 | A1 | 7/2009 |
| WO | 2015/069549 | A1 | 5/2015 |
| WO | 2015/183977 | A2 | 12/2015 |

* cited by examiner

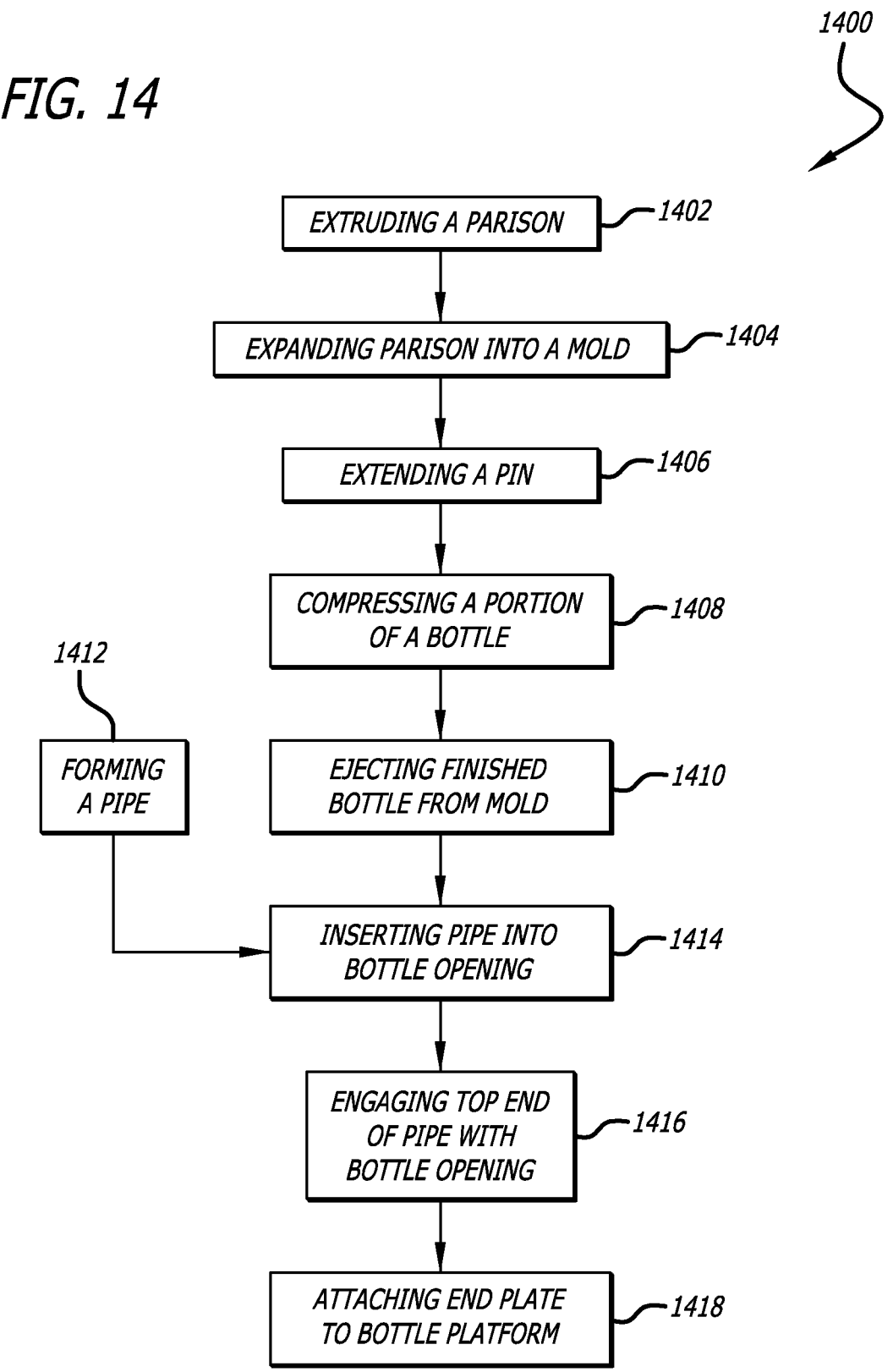

REAGENT BOTTLE WITH ASPIRATION PIPE

CROSS REFERENCE TO RELATED APPLICATIONS

This application claims the benefit of U.S. provisional patent application No. 62/003,453, filed May 27, 2014, the entire disclosure of which is incorporated herein by reference.

FIELD

This invention relates generally to reagent containers for use with automated analyzers.

BACKGROUND

Automated chemical analyzers, such as clinical chemical analyzers, perform tests by combining reagents with samples. Analyzers hold reagents in reagent containers on board the analyzer for transfer by pipetting. Analyzers may present reagent containers at a pipetting location in rapid succession to achieve high test throughput. This rapid presentation can cause reagents in large reagent containers to slosh. Reagent sloshing may cause a variety of problems including pipetting errors, level sensing errors, and pipette contamination.

Reagent containers are rarely completely full. Even freshly opened containers usually have an unfilled headspace into which reagents can move. As an analyzer uses reagents the amount of headspace increases. This unfilled volume allows reagents to shift position within reagent containers in response to applied forces.

Moving reagent containers applies forces to reagents inside. For example, when an analyzer presents reagent containers on a rotating turntable, the reagents in the containers are subject to a variety of inertial forces. These forces include centrifugal force that accelerates the reagents radially outwardly, Coriolis force that accelerates particles of fluid perpendicularly to their velocity, and angular acceleration and deceleration that accelerate reagents in the reverse of the direction of the turntable acceleration. Reagents move within reagent containers in response to these forces. This motion is manifested as waves with amplitude, spectrum, and duration dependent on reagent container geometry, on fill level, on speed of motion and acceleration, and on reagent fluid parameters. Reagent waves slosh through the reagent container, altering the local height of reagent even after motion stops.

Prior reagent containers include a variety of pipes and baffles to reduce the effect of reagent sloshing, but these suffer from shortcomings including inadequate slosh protection, bubble and aerosol formation, high dead volume, blocking of openings with reagent films, and limitations on bottle fill rate. Some art includes a vertical pipe that takes up the entire opening of a blow-molded bottle and includes a ventilation hole within the vertical pipe wall (see FIG. 1 PRIOR ART). Such ventilation holes are susceptible to blocking by a liquid film of surfactant-containing reagents. The external surfaces of blow-molded bottles of the prior art are controlled by contact of an expanding parison with the walls of a mold cavity. The internal surfaces are not dimensionally controlled; they result from flow patterns of softened polymer in contact with colder metal of the mold cavity. Parting lines resulting from intrusion of polymer material between parting surfaces of a moldbase during molding may produce sink marks or other deformations on the inner surface of bottle overlaying the parting line. Parting lines may commonly occur along a midline of the bottle, which is a preferred location for fluid transfer operations. Consequently, the internal surfaces of blow-molded bottles are of varying thickness and surface finish. The walls are not sufficiently smooth and flat for consistent attachment of a pipe at a fixed position, particularly if that position overlays parting lines or other mold geometry. Other art includes pipes with flow resistance elements near the bottom that retard fluid transfer in response to transient forces. Such flow resistance elements increase inaccessible dead volume in the reagent container. There is therefore a need to provide a reagent container not subject to these shortcomings.

SUMMARY

In some embodiments, described are reagent containers including a bottle and a pipe disposed within the bottle. In some embodiments, the bottle is a blow-molded bottle. In other embodiments, the bottle can be an elongated blow-molded bottle. The structure of the bottle can include, but is not limited to a bottom wall or elongated base, a top wall or a cover, a side wall, and an end wall. In some embodiments, the bottom wall is opposed to the top wall and/or the end wall is shorter than the side wall. The end wall disposed near one end of the bottom wall connects the bottom wall to the top wall. The top wall includes a bottle opening for fluid filling and removal. The bottom wall includes a controlled surface including a flat platform surrounded by a rim disposed opposite the bottle opening.

Other embodiments comprise a bottle including a top wall, a first side wall, and a second side wall, the top wall having an opening, and the first side wall and the second side wall connected to the top wall. The bottles can include a pipe disposed in the bottle opening, wherein the pipe includes a central axis, a top end, a bottom end, and a tube wall disposed about the central axis and connecting the top end to the bottom end. In some embodiments, the tube wall has a first straight segment and a second straight segment extending parallel to the central axis. In some embodiments, the first straight segment is disposed substantially parallel to the first side wall and the second straight segment is disposed substantially parallel to the second side wall.

The pipe can include an open top end, a bottom end, and a tube wall connecting and/or extending from the top end to the bottom end. The tube wall has an aperture adjacent the bottom end. The pipe is disposed in the bottle and affixed to the bottle with the top end positioned within the bottle opening and the bottom end secured to the controlled surface. The aperture faces and/or is disposed towards the end wall.

In some embodiments, the bottle is substantially wedge-shaped with a wide end and a narrow end. The end wall connects diverging side walls at the wide end. The bottle opening may be disposed close to the wide end and may include a neck with external threads. The pipe may include converging wall segments disposed substantially parallel to the side walls. In some embodiments, the bottle includes a top wall, a bottom wall opposed to the top wall, and side walls connecting the top wall to the bottom wall. The top wall has an opening, and the bottom wall has a controlled surface including a flat platform surrounded by a rim. In one embodiment, the bottom wall has a controlled surface surrounded by a raised rim, wherein the controlled surface is disposed inside the bottle and opposite the opening. When the bottle is upright, the controlled surface aligns directly below the opening. In further embodiments, the bottle includes a parting line resulting from the formation of the bottle, and the controlled surface overlays the parting line.

In other embodiments, the bottle is substantially wedge-shaped and the side wall includes a first converging wall, a second converging wall, and an end wall connecting the first converging wall to the second converging wall, and wherein the tube wall has a first straight segment and a second straight segment, wherein the first straight segment is disposed substantially parallel to the first converging wall and the second straight segment is disposed substantially parallel to the second converging wall.

The pipe can include a tube with two ends: one end is open and the other partially closed by an endplate. For example, in one embodiment, the pipe can includes a tube wall connecting an open top end and a bottom end, wherein the bottom end includes an endplate partially closing the bottom end and an aperture in the tube wall adjacent the bottom end. The pipe inserts into the bottle with the open end positioned within the bottle opening and the endplate attached to the controlled surface. In one embodiment, the pipe is affixed to the bottle by attaching the endplate to the controlled surface.

In one embodiment, the pipe has a diameter between about one-fifth and about one-third of the distance between the first converging wall and the second converging wall measured at the opening.

The pipe may have a central axis with a tube wall formed about the central axis to define a lumen within the pipe. The tube wall may include multiple segments, which may be straight or curved, and these segments extend along the length of the pipe parallel to the central axis. In some embodiments, the tube wall includes three straight segments and an arcuate segment. Any or all of the segments may include one or more ribs or a plurality of ribs projecting and/or extending outwardly a short distance, such as 1 to 3 mm, from the outer surface of the tube wall. When inserted into the opening of the bottle, the ribs interfere with the bottle at the opening to hold the pipe in place. In other words, the pipe can be affixed to the bottle by an interference fit between the plurality of ribs and the opening. The tube wall diameter (not including the ribs) may be smaller than the opening so that when the pipe is installed, the gaps between the tube wall and the opening, as separated by the ribs, form vents to the interior of the bottle. In one embodiment, the tube wall, at least one of the ribs, and the opening defines a vent passage outside of the pipe. Such vents are parallel to the lumen and form separate passages from the lumen. Two of the straight segments may be substantially parallel to respective side walls of the bottle.

In some embodiments, the bottle includes an end wall connected between the first side wall and the second side wall, the end wall shorter than the first side wall and shorter than the second side wall. The pipe can further include an aperture in the tube wall, wherein the aperture can be oriented towards the end wall.

In other embodiments, the bottle includes a bottom wall disposed substantially parallel to the top wall, the bottom wall connecting the first side wall, to the second side wall, and to the end wall, the bottom wall having a circular platform surrounded by a raised rim, wherein the platform is opposed to the opening. The bottom end of the pipe can include an endplate partially closing the bottom end and the endplate can be attached to the platform.

In one embodiment, the tube wall includes an arcuate segment between the first straight segment and the second straight segment which can also serve as a connector. In some embodiments, at least one of the plurality of ribs extend outwardly from the arcuate segment.

In other embodiments, described are methods of producing a reagent container. The methods can include processes of forming a bottle, such as a blow-molded bottle, that includes steps of forming the bottle. The bottle can include an opening and a platform opposed to the opening, or can include an opening and a controlled surface forming a platform opposed to the opening. The controlled surface may overlay a parting line created during formation of the bottle.

The forming process can include extruding a parison having a tubular body with an inlet and clamping the parison into a hollow mold, where the mold has a wall opposed to the inlet.

In some embodiments, the parison is expanded into a mold having a wall opposed to an inlet, wherein an expanded parison forms the bottle and the inlet forms the opening; a pin having a face is then extended through the inlet to position the face a predetermined distance from the wall; and further, a portion of the bottle is compressed between the pin face and the wall forming the platform surrounded by a raised rim.

Then the parison is expanded to contact the internal walls defining the hollow, and extending a pin having a flat face through the inlet to position the flat face a predetermined distance from the bottom wall. The flat face can be flat and circular. The predetermined distance from the wall can be less than about 1 mm. The pin compresses and displaces the plastic material of the parison, causing the polymer to flow outward from the limited volume between the pin face and the bottom wall of the mold. The flat face can hold the plastic material in place against the bottom wall of the mold thereby forming a controlled surface surrounded by a raised rim. In some embodiments, the raised rim extends about 1 mm to about 3 mm above the controlled surface. In some embodiments, this controlled surface surrounded by a raised rim is referred to as a flat platform. Further, the controlled surface can be substantially flat such as within about 0.2 mm.

In further embodiments, the portion of the bottle compressed between the pin face and the wall can overlay a parting line in the mold. The mold can define a wedge-shaped cavity having a narrow end forming an end wall of the bottle.

The described methods can further comprise: positioning a pipe through the opening, the pipe including an open end, a bottom end partially closed by an endplate, and a tube wall extending from the open end to the bottom end; and attaching the endplate to the platform.

The method may additionally include a step of positioning a pipe through the opening in the bottle to form the reagent container, where the pipe has an open end, a second end partially closed by an endplate, and a tube wall extending between the open end to the second end.

The method in some embodiments includes attaching the endplate to the controlled surface or the flat platform of the controlled surface. In some embodiments, the endplate may include an energy director, and the method includes attaching the endplate to the controlled surface or the flat platform of the controlled surface, for example, by welding such as ultrasonically welding the two parts. Thus, in some embodiments, the endplate is ultrasonically welded to the controlled surface.

In some embodiments, the tube wall includes an aperture adjacent the bottom end, wherein the endplate includes an energy director, and wherein the step of positioning the pipe through the opening includes aligning the aperture toward the bottle end wall.

In some embodiments the pipe may have one or more ribs or a plurality of ribs extending outwardly from the tube wall and the step of positioning the pipe through the opening may include frictionally engaging the pipe within the opening so that the rib spaces a portion of the tube wall from the opening to define a vent passage. Further, the pipe at the open end can frictionally engage the bottle at the opening to retain the position and orientation of the pipe within the bottle.

BRIEF DESCRIPTION OF THE DRAWINGS

FIG. 14 is a flowchart of an example embodiment of a production process described herein.

DETAILED DESCRIPTION

Figure 1:
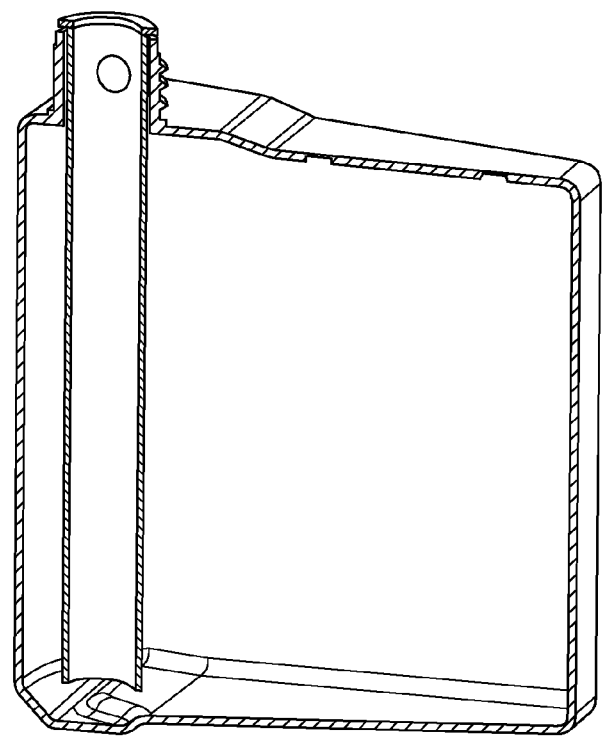
FIG. 1 is a three-dimensional view of a prior art reagent container with a segment of wall removed to reveal internal structure.

FIGS. 2-12 show reagent container 100 including bottle 102 and pipe 104. Pipe 104 inserts into and can be affixed to bottle 102.

Bottle 102 can include an elongated base, a cover, and walls.

FIGS. 2-6 illustrate an embodiment of bottle 102 as having a generally wedge-shaped hollow body. Elongated base 106 forms the bottom of upright bottle 102. As visible in FIG. 3, when bottle 102 is upright, walls extend vertically from base 106 toward cover 108. Base 106 is bounded by converging side walls 110,110', end wall 112, and inner wall 114. Base 106 may also include anchor region 116 and legs or other elements to support base 106 in a predetermined manner when resting on a flat surface or when inserted into a movable container platform.

Base 106 may be roughly planar. Roughly planar means that the deviations from planarity are small compared with the extent of base 106. Roughly planar includes conformations of the base 106 having features that support the base so that, when bottle 102 is standing upright, base 106 slopes toward a low point. This reduces the volume of contained liquid that is inaccessible to pipetting through analyzer probe 118. Features that support base 106 may include the reverse side of the anchor region described below, skirting walls that extend below portions of base 106 at the edges (not shown), and one or more attached legs or ribs or a plurality of legs or ribs.

The upper aspect of the base 106 may slope toward the area of the bottle from which the analyzer probe 118 draws reagent. The embodiment of FIG. 2 includes a slope 120 towards the portion of the base 106 disposed directly beneath the bottle opening (best visible in FIG. 3). Slope 120 can have an angle of about 5 degrees, about 10 degrees, about 15 degrees, about 20 degrees, about 25 degrees, about 30 degrees, at least about 5 degrees, at least about 10 degrees, at least about 15 degrees, at least about 20 degrees, between about 5 degrees and about 20 degrees, or between about 5 degrees and about 30 degrees. This slope 120 can reduce inaccessible fluid ("dead volume") by causing reagents to flow toward point or region of aspiration 122. The lower aspect of base 106 roughly parallels the upper aspect and may include supports such as hollow legs 124 and 126 disposed toward side walls 110,110'. In other locations, the lower aspect of base 106 may not conform to the upper aspect, such as at ridge 128 that extends from the lower aspect of base 106 near inner wall 114. Ridge 128 elevates base 106 near inner wall 114 to provide the slope disclosed above.

Figure 6:
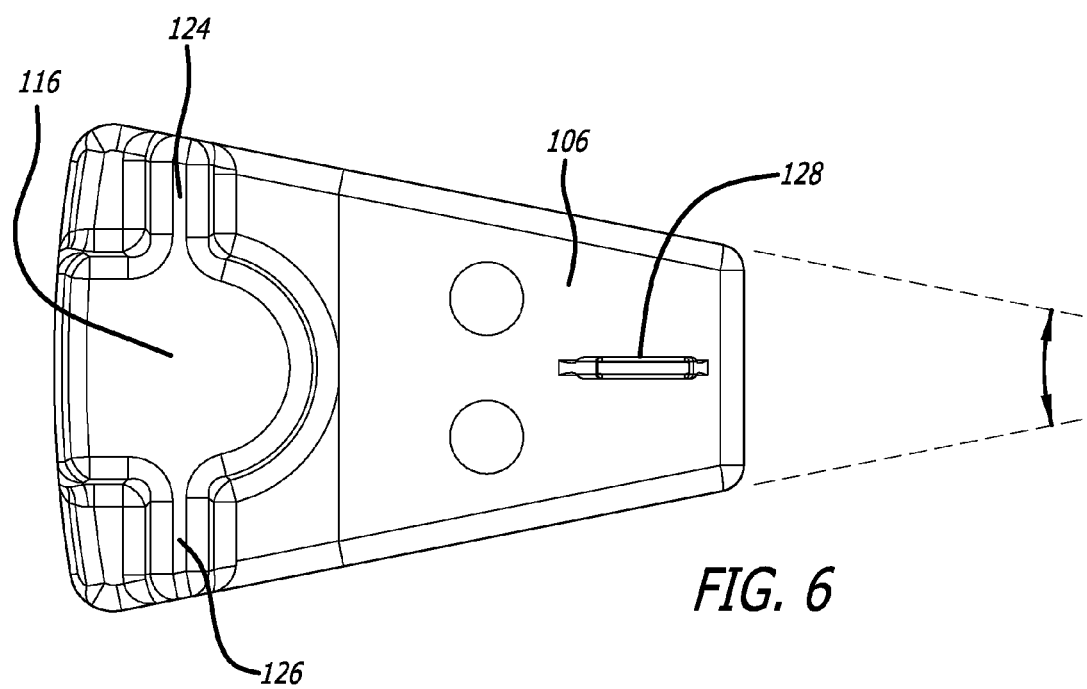
FIG. 6 is a bottom view of the embodiment of FIG. 2.

Base 106 also includes anchor region 116 best visible in FIG. 6. The interface of anchor region 116 includes circular flat platform 130 surrounded by rounded rim 132. Anchor region 116 is disposed opposite the opening in the cover to align with probe 118 during aspiration. As described above, anchor region 116 is disposed at or near the lowest part of bottle 102 (when bottle 102 is upright), and at least a portion of the upper aspect of base 106 slopes toward anchor region 116. Flat platform 130 can advantageously provide a controlled surface to attach the bottom of pipe 104 so as to minimize dead volume within reagent container 100. Platform 130 is close to or substantially horizontal when bottle 102 is upright to ensure perpendicularity to the long central axis of inserted pipe 104. This horizontal disposition and flatness of platform 130 helps assure good attachment to pipe 104. In one example embodiment, platform 130 is flat to within 0.2 mm and has thickness of 1.3 mm+/−0.2 mm. In some embodiments, the thickness of platform 130 may range up to about 2 mm, but thinner embodiments up to about 1 mm advantageously reduce material consumption and molding cycle time.

Rim 132 surrounds platform 130 and can be 1 to 3 mm higher than the controlled surface forming platform 130. Rim 132 helps in centering pipe 104 during its insertion and helps to limit outflow of reagent from platform 130, thereby reducing dead volume. Controlled surface forming platform 130 may overlay a parting line or other raised geometry of the blow-molded bottle.

Cover 108 opposes base 106. Opposes means that cover 108 is disposed substantially parallel to or on the same plane as base 106 and spaced a distance apart from base 106, where the distance is of similar magnitude to the extent of base 106. Substantially parallel includes a range at least encompassing parallel to base 106 and parallel to a flat surface supporting base 106 when bottle 102 is standing upright.

Cover 108 includes opening 134 and may include a neck. Cover 108 is of similar extent to base 106 and connects to it by walls. Cover 108, base 106, and connecting walls define the hollow interior of bottle 102, which is closed except at opening 134. In some embodiments bottle 102 may hold more than one reagent in compartments separated by interior walls. In such embodiments, each compartment may have a separate opening.

Opening 134 may be circular for ease of closure and manufacture. The neck may surround opening 134 and extend upwards from the balance of cover 108 as a cylindrical wall. The neck may include external threads 136 to conform to a removable cap (not shown). In other embodiments, a membrane seal may cover opening 134. In still other embodiments, a friction fitting or other appropriate fitting may be used.

The walls of bottle 102 are configured to connect base 106 to cover 108. Walls include end wall 112, side walls 110, 110', and inner wall 114. In the wedge-shaped embodiments illustrated, side walls 110,110' converge from relatively wide end wall 112 toward narrower inner wall 114. Other embodiments may include side walls that converge without inner wall 114 to meet one another forming a triangular bottle or parallel side walls forming a substantially rectangular bottle.

Figure 9:
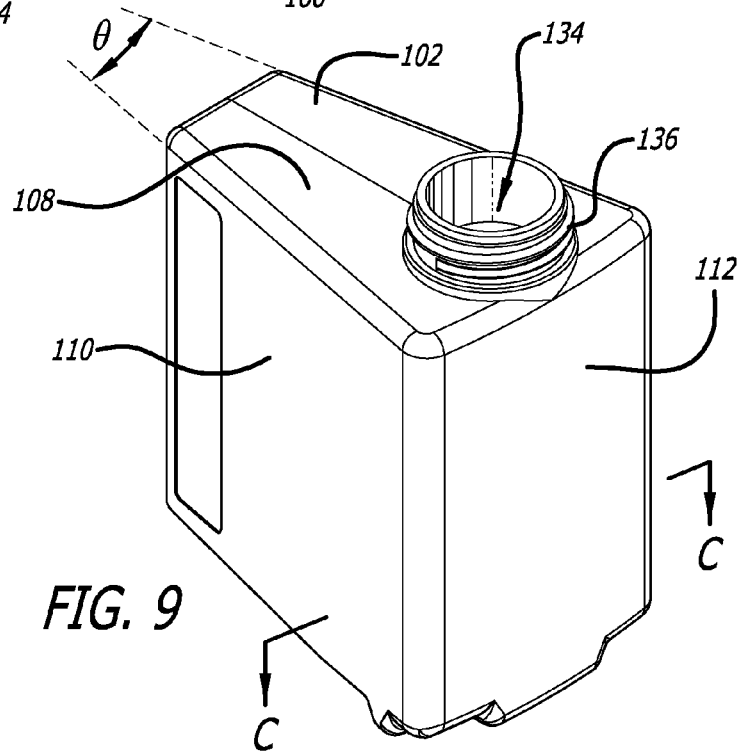
FIG. 9 is a perspective view a first embodiment of the bottle described herein shown with the pipe removed.
Figure 10:
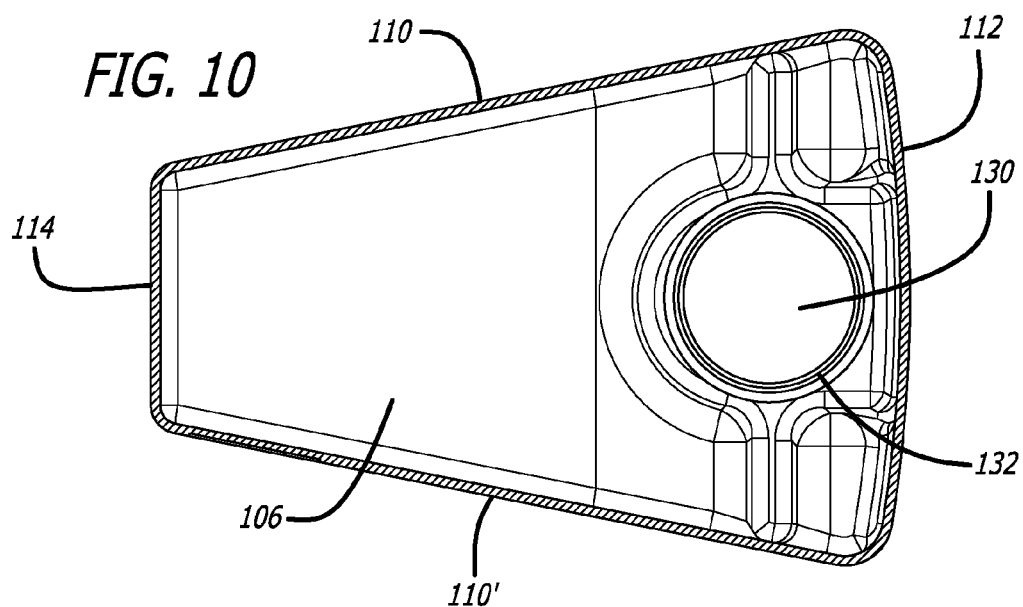
FIG. 10 is a top-sectional view of the bottle of FIG. 10 along the line C-C of FIG. 9.

The side walls can converge (as illustrated in FIG. 9) at an angle of about 5 degrees, about 10 degrees, about 15 degrees, about 20 degrees, about 25 degrees, about 30 degrees, about 35 degrees, about 40 degrees, about 45 degrees, at least about 5 degrees, at least about 10 degrees, at least about 15 degrees, at least about 20 degrees, between about 5 degrees and about 45 degrees, or between about 20 degrees and about 45 degrees.

The convergence of side walls 110,110' can allow multiple bottles to be arranged in a circular configuration with their openings oriented around a circle. This bottle orientation can allow rapid sampling using probe 118. In other embodiments, bottles can be used without arranging them in a circular configuration. In other words bottles described herein can be used for individual rapid sampling using probe 118.

When reagent container 100 is upright, base 106 is beneath cover 108, and end wall 112 and pipe 104 stand vertically. In use, the upright reagent container holds a fluid or suspension, such as a reagent liquid. Reagent container 100, and others of similar construction, mounts to a moving device that sequentially presents desired fluids to an aspiration location in an analyzer. The moving device is typically a turntable so that reagent containers may rotate about a central axis, but some analyzers may move reagent containers using rectilinear or other motions. The time to position a reagent container contributes to analyzer throughput; quick positioning is desirable. Quick positioning requires fast movement with high rate acceleration and deceleration that can cause sloshing of the contents within the reagent container.

In some embodiments reagent container 100 is generally wedge-shaped so that reagent container 100 and other containers of similar shape may be disposed in a space-filling arrangement on a rotatable disk. This advantageously allows a single motion axis to position a selected reagent container adjacent an aspiration point for reagent transfer. In such embodiments, end wall 112 is disposed toward the outside of the disk and side walls 110, 110' project radially and converge toward the disk center. End wall 112 may be flat or curved. The illustrated curved end wall 112 provides extra reagent capacity with high strength while fitting within the profile of a circular turntable.

Figure 7:
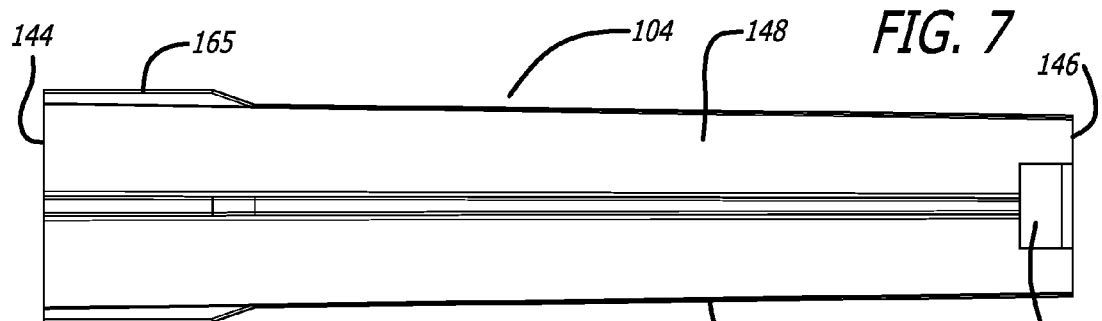
FIG. 7 is a side view of a first embodiment of the pipe described herein shown removed from the bottle.
Figure 8:
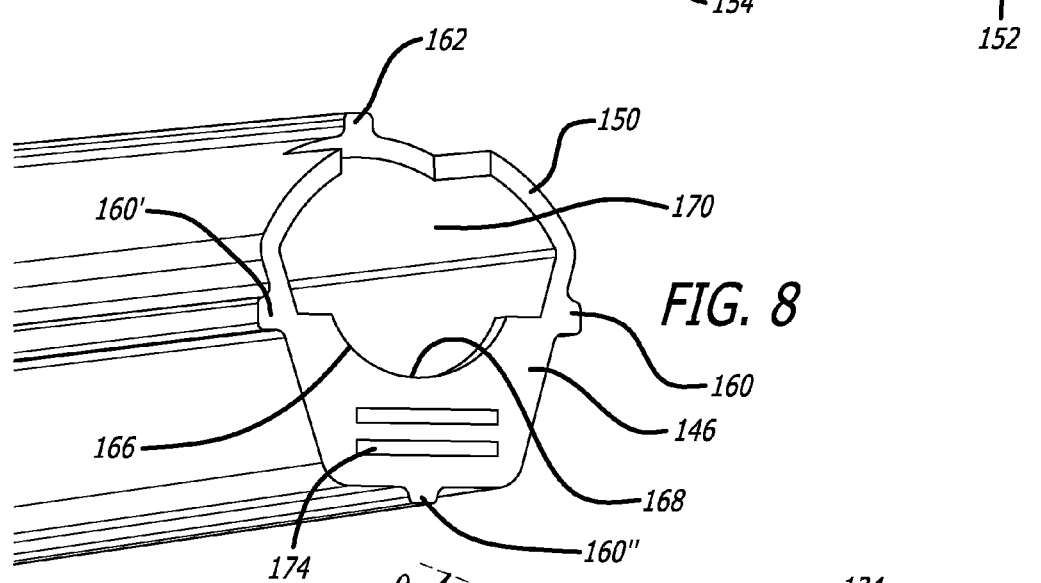
FIG. 8 is an end perspective view of the pipe of FIG. 7.

FIGS. 7 and 8 show an embodiment of pipe 104 as an elongated hollow tube that includes first or top end 144, a second or bottom end 146, and tube wall 148 extending between top end 144 and bottom end 146. Pipe 104 tapers from relatively wide top end 144 to relatively narrow bottom end 146. This taper simplifies molding and insertion of pipe 104. Pipe 104 inserts into opening 132 of bottle 102 so that pipe 104 is disposed vertically when reagent container 100 is upright. When assembled, top end 144 sits within opening 132, and bottom end 146 contacts platform 130.

The size of pipe 104 can eliminate wave motion on the reagent surface. A relatively large liquid volume within pipe 104, as in this design, in conjunction with the aperture size and position provides good wave motion suppression. Pipe diameters may depend upon bottle width in conjunction with the size and positioning of aperture described below. Pipe 104 can have diameter between about ⅕ (one-fifth) and about ⅓ (one-third) of the distance between the first converging wall and the second converging wall measured at the end wall 112. In some embodiments, a pipe diameter of about ⅓ of the length of end wall 112 substantially eliminates unstable reagent surface behavior within pipe 104.

Tube wall 148 defines a lumen and is formed of relatively thin material relative to its extent. In some embodiments, tube wall 148 includes arcuate segment 150, straight segments, aperture 152, and ribs 154. Straight segments may include inner segment 156 and connecting segments 158, 158'. Inner segment 156 is disposed opposite arcuate segment 150. The edges of inner segment 156 connect via connecting segments 158,158' to the edges of arcuate segment 150. Connecting segments 158,158' may be of equal length and connect to inner segment 156 at equal angles so that tube wall 148 is symmetrical about the plane containing the long axis of pipe 104 and passing through the midlines of arcuate segment 150 and of inner segment 156. This complex profile forms a stiff tube with residual openings of controlled shape surrounding pipe 104 when pipe 104 inserts into opening 134.

When pipe 104 is inserted into bottle 102 and oriented so that arcuate segment 150 is adjacent end wall 112, connecting segments 158,158' each extend substantially parallel to the nearer of side walls 110,110'. This parallel disposition of connecting segments 158,158' and side walls 110, 110' helps dissipate the sloshing effect of reagent waves away from aperture 152, reducing the effect of wave motion on reagent height within pipe 104. Substantially parallel here encompasses exactly parallel and angles up to about 20 degrees from parallel. In some embodiments, connecting segments 158,158' are disposed at an angle of about 5 degrees from the nearer of side walls 110, 110'.

Aperture 152 pierces tube wall 148 and extends from bottom end 146 upward. In the illustrated embodiment, aperture 152 pierces arcuate segment 150 symmetrically about the midline of arcuate segment 150. Two straight edges disposed vertically (toward top end 144) and a perpendicular top edge define aperture 152 as substantially rectangular. Aperture 152 may extend from about 3 mm to about 5 mm toward top end 144 and may have width from about 6 mm to about 8 mm. In some embodiments, aperture 152 measures about 3 mm toward top end 144 and about 6 mm in width. These dimensions of aperture 152 advantageously cooperate with height of rim 132 to reduce the rate of reagent flow between pipe 104 and portion of bottle 102 external to pipe 104. This flow rate reduction helps reduce the effect of reagent container motion on reagent height within pipe 104.

One or more stiffening ribs 154, 154' may extend substantially along the entire length of pipe 104. In the illustrated embodiment, three long ribs 160, 160', 160" extend from top end 144 to bottom end 146. Short rib 162 extends from top end 144 to aperture 152. Ribs 154 stiffen pipe 104, allowing relatively thin thickness of tube wall 148.

Ribs 154 strengthen tube wall 148, define vents 164, and help secure pipe 104 within bottle 102. Ribs 154 may extend from the outer aspect of tube wall 148 different distances in different locations. Upper rib portions 165 may extend farther (a total of about 2 mm) from tube wall 148 to permit low friction insertion of bottom end 146 into bottle 102 while providing high friction for interference fit when pipe 104 fully inserts into bottle 102. This aids assembly by reducing required force for most of the insertion operation while maintaining a tight fit at full insertion depth. The relatively thin tube wall 148 (or neck 136) may deform so that pipe 104 fits within neck 136 tightly. This interference fit ensures that bottle 102 holds pipe 104 securely at the bottle neck position.

Bottom end 146 includes endplate 166 disposed perpendicularly to the long axis of pipe 104. Endplate 166 only partially closes bottom end 146. Endplate 166 may cover less than about half of the area of bottom end 146 and connects the terminus of inner segment 156 to proximal portions of the termini of connecting segments 158, 158'. The free border of endplate 166 includes arcuate cutout 168 curved in the opposite direction from arcuate segment 150. The remainder of bottom end 146 is open portion 170, which is contiguous with aperture 152. The open space between arcuate cutout 168 and arcuate segment 150 advantageously provides a roughly circular locus 172 (see FIG. 2) to accommodate tolerance stack up in positioning or straightness of probe 118 during pipetting.

In some embodiments, endplate 166 may be attached to platform 130 to secure pipe 104 in desired orientation and position. Applicable attachment methods include welding (including ultrasonic, vibration, thermal, and induction welding), adhesives, solvent bonding, fastening, or a "snap" feature formed into the mating parts. Endplate 166 may include one or more energy director 174 on its lower aspect (most distal from top end 144). Energy director 174 can provide a reduced surface area for attaching pipe 104 to platform 130. Energy director 174 may be any of a variety of shapes suitable for the attaching (e.g., welding) process. In the illustrated embodiment, energy director 174 comprises two parallel bosses disposed parallel to inner segment 156 and extending perpendicularly from endplate 166 from about 0.02 mm to about 1 mm.

In other embodiments, the friction fit of pipe 104 within neck 136 suffices to retain the position of bottom end 146 adjacent platform 130. This friction fit also maintains the orientation of pipe 104 so that arcuate segment 150 and aperture 152 are disposed toward end wall 112. As discussed above, the friction fit may include an interference fit between ribs 154 and neck 136 that causes tube wall 148 or neck 136 to deform to accommodate the interference.

The orientation of pipe 104 within bottle 102 can be important to reduce reagent wave motion and turbulence in pipe 104. In some embodiments, aperture 152 faces end wall 112. This can advantageously reduce the effect within pipe 104 of inertial forces arising from reagent container movement. Pipe 104 may be oriented from the upper end by aligning short rib 162 toward end wall 112. When pipe 104 is inserted into bottle 102 and oriented so that arcuate segment 150 is adjacent end wall 112, connecting segments 156 each extend substantially parallel to the nearer of side walls 110, 110'. This near parallel disposition of connecting segments 156 and side walls 110, 110' helps dissipate the sloshing effect of reagent waves away from aperture 152, reducing the effect of wave motion on reagent height within pipe 104.

Engagement of upper rib portions 166 with neck 136 defines vents 164 between tube wall 148 and neck 136. Vents 164 provide a path for pressure equalization between atmosphere and reagents held within the portion of bottle 102 outside of pipe 104. Vents 164 allow air to pass out of the bottle during filling and into the bottle during reagent aspiration. Vents 164 also ensure that reagents on both sides of tube wall 148 are subject to common liquid pressure equilibrium to maintain the same reagent height. Some reagents may contain surfactants that could form films across small openings. The extent of ribs 154 (projecting about 2 mm from outer aspect of tube wall 148) in combination with the trapezoidal shape of pipe 104 helps avoid closure of vents 164 by reagent films.

Figure 2:
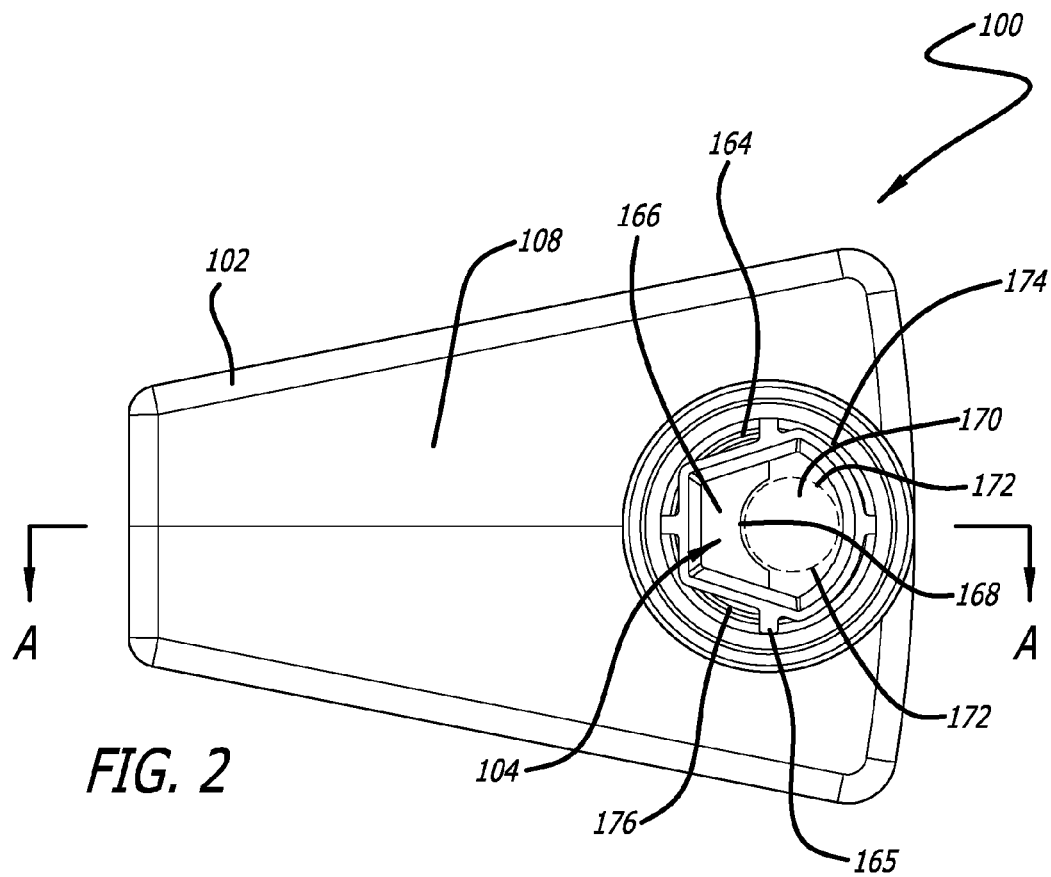
FIG. 2 is a top view of a first embodiment of the reagent container.
Figure 3:
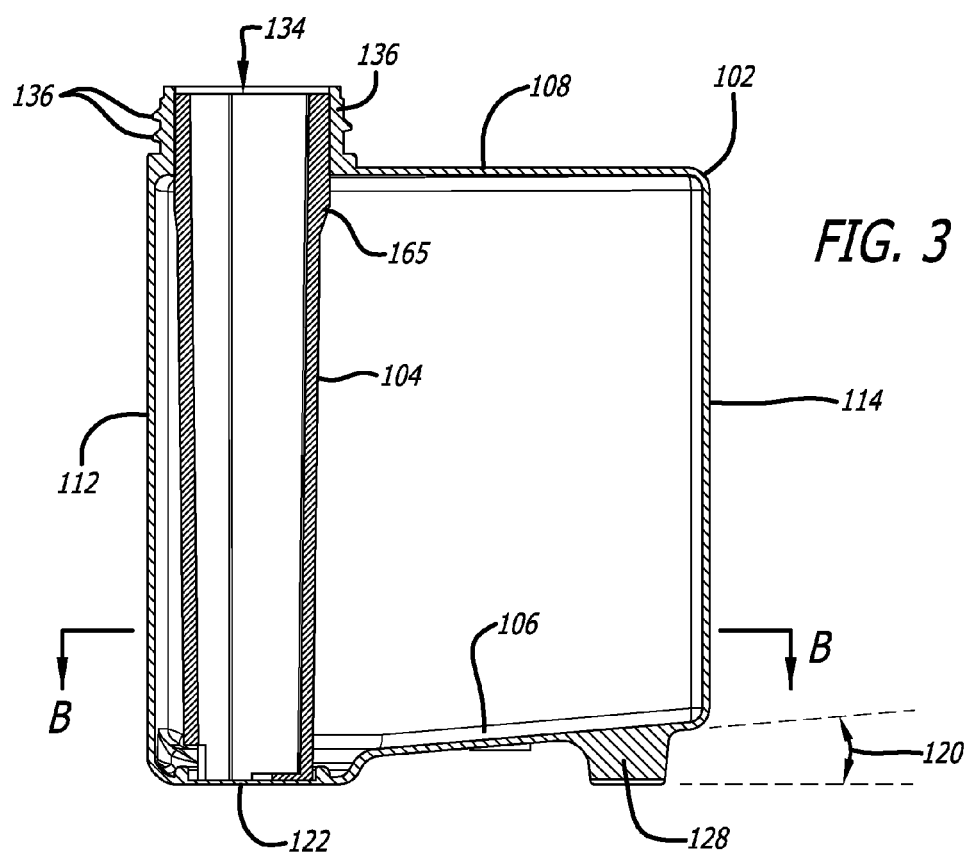
FIG. 3 is a side-sectional view of the embodiment of FIG. 2 along the line A-A of FIG. 2.
Figure 4:
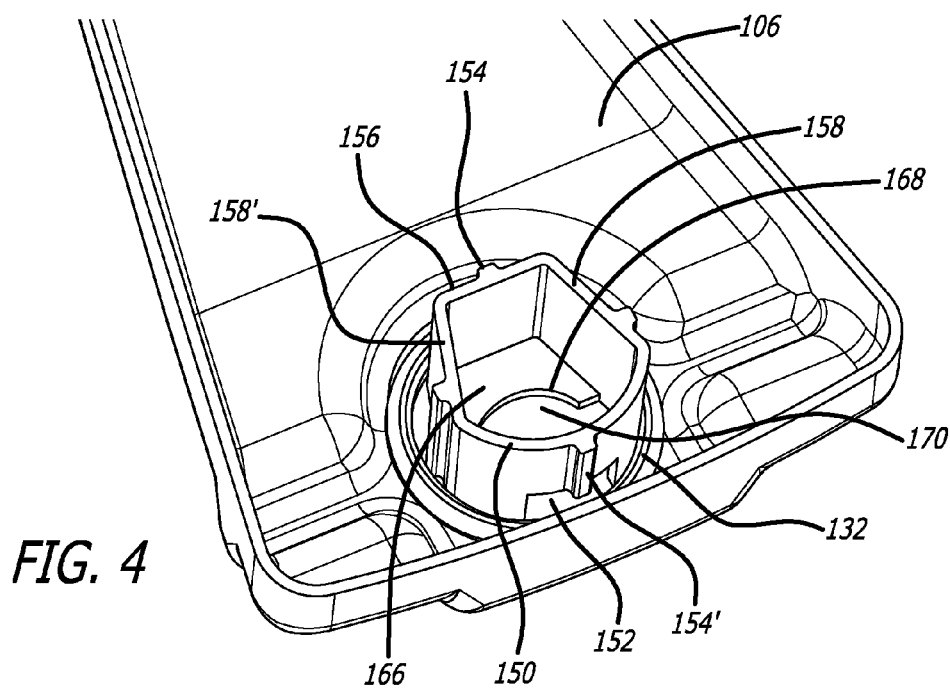
FIG. 4 a perspective view of the embodiment of FIG. 2 sectioned along line B-B of FIG. 3.
Figure 5:
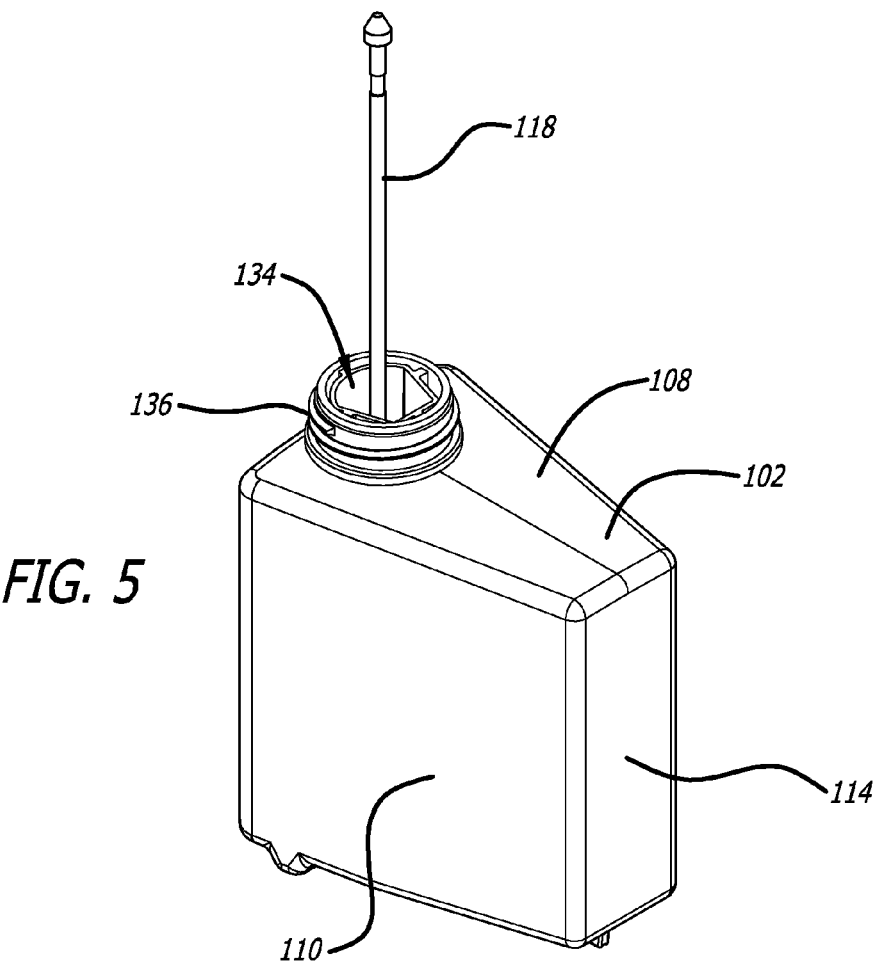
FIG. 5 is a perspective view of the embodiment of FIG. 2.

Vents 164 may include curved vents 174 and straight vents 176. Vents 164 span the gap between the internal surface of neck 136 and tube wall 148 and are bounded radially by upper rib portions 165. Curved vents 174 border at least a portion of arcuate segment 150; straight vents 176 border straight segments 158, 158'. FIG. 2 shows an embodiment including two curved vents 174 and two straight vents 176 symmetrically disposed within opening 132.

Also described are methods of fabricating reagent container 100 by a combination of blow molding of bottle 102, injection molding of pipe 104, and post molding assembly steps. Conventional blow molding is inadequate to produce an interior surface in anchor region 116 with suitable tolerance. Injection molding may produce acceptable tolerances, but requires bottle closure operations that are costly and problematic. A modified blow molding process has been developed that can provide acceptable tolerances at low cost using conventional blow molding materials. In some embodiments, the blow molding material is a polymer such as high density polyethylene.

A conventional extrusion-blow molding process begins with melting down a selected plastic and forming it into a parison. A parison is a tube-like piece of plastic with a hole in one end through which compressed air or other fluid can pass. The parison extrudes between separated parts of a mold that includes a hollow cavity. The mold closes onto the parison, which then inflates so that the outside surfaces abut the bounding walls of the cavity. Opening the mold releases the part.

The extrusion-blow molding process controls exterior surfaces through contact with the walls of the mold, but interior surfaces may not be as well controlled. The moldbase typically closes on a portion of the parison so that the moldbase separation surfaces image as raised parting lines on the ejected part. The geometry of interior surfaces opposite the parting lines frequently include sink marks or other irregularities due to variable thicknesses and differential cooling rates.

The herein described process can provide particular benefits when an anchor region lies atop a parting line of the bottle because these areas are particularly vulnerable to irregular surface conformation.

Figure 11:
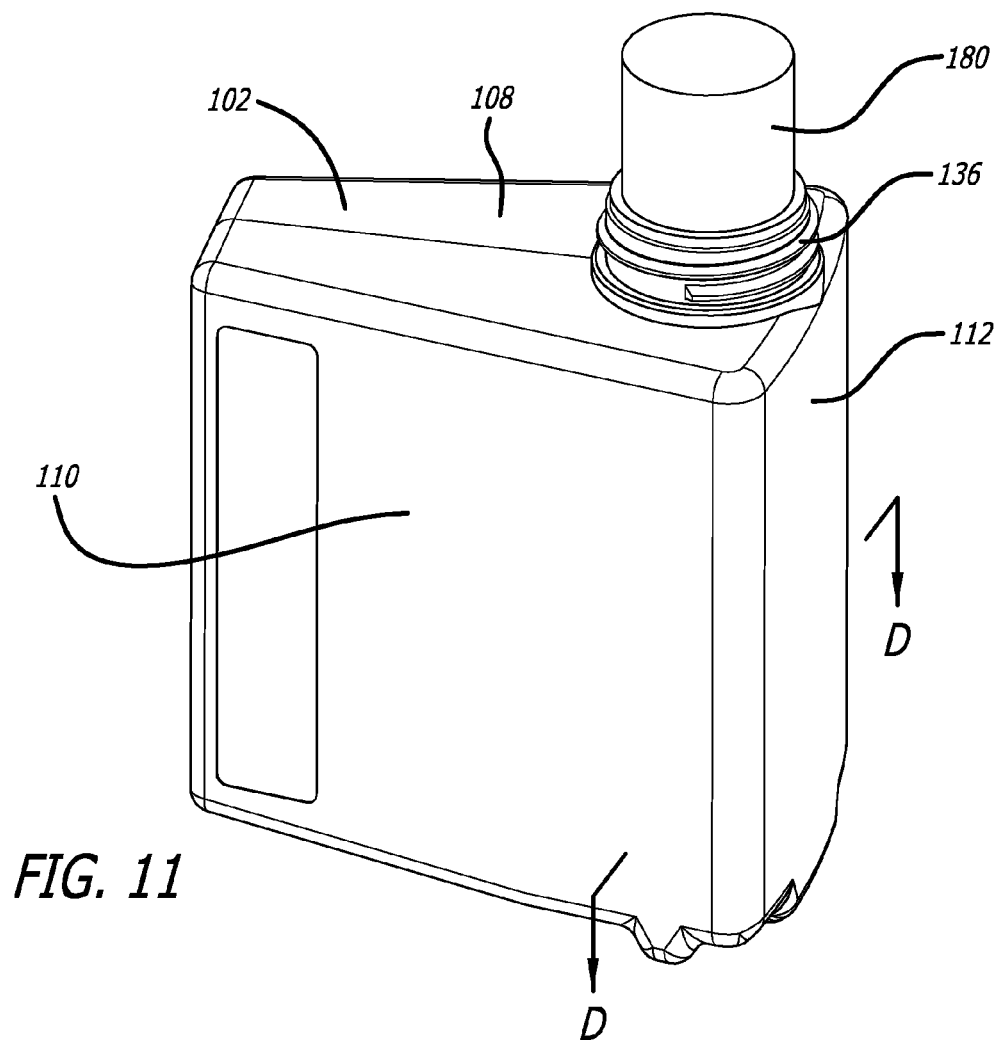
FIG. 11 is a perspective view of the bottle described herein shown during fabrication according to an embodiment of the method described herein.
Figure 12:
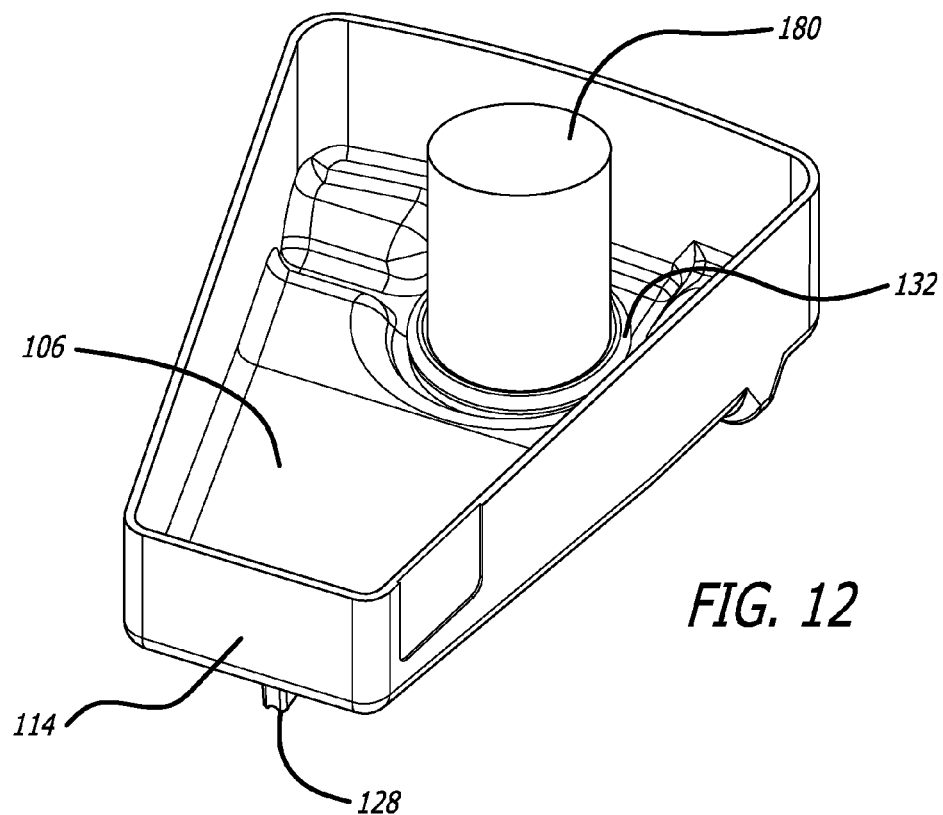
FIG. 12 is a perspective view of the embodiment of FIG. 11 sectioned along line D-D of FIG. 11.
Figure 13:
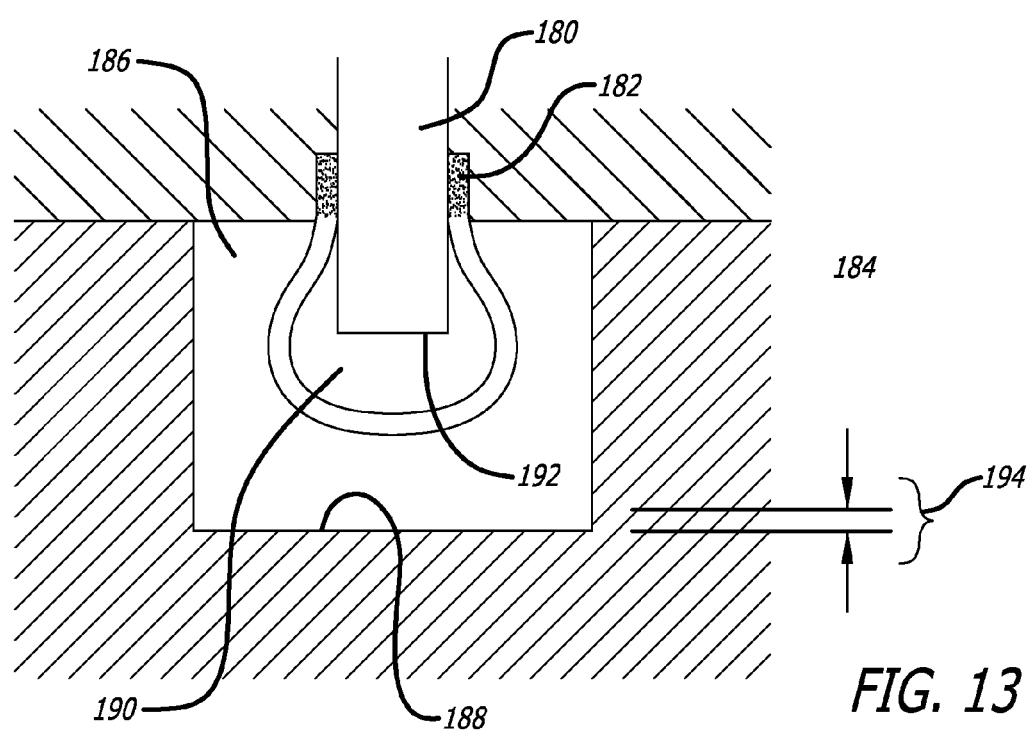
FIG. 13 is a diagrammatic sectional view of an embodiment of a portion of the production process.

An extrusion blow molding process includes steps of parison extrusion, clamping the extruded parison into a hollow mold, expansion of the parison into the mold, and extension of a pin having a formed face through the parison opening while the material remains malleable or plastic. FIGS. 11 through 13 show bottle during production with pin 180 extending through opening 132 and contacting base 106 to form platform 130 and rim 132. A conventional extrusion-blow molding process does not include an extended pin as described herein.

As illustrated in FIG. 13, once parison 182 is formed, mold 184 clamps parison 182 in a hollow cavity 186 that conforms to the desired external shape of the bottle, such as a wedge-shaped cavity. Mold 184 includes bottom wall 188 opposite the inlet that corresponds to the anchor region of the bottle. Pressurized air or other fluid expands parison 182 within hollow cavity 186 to form a hollow container 190 as in conventional blow molding. After expansion, but while the polymer material is still plastic, pin 180 having a flat face 192 perpendicular to the pin's axis extends through the inlet to position face a predetermined distance 194 from bottom wall 188. In some embodiments, the predetermined distance can be less than about 3 mm, less than about 2 mm, or less than about 1 mm.

Flat face 192 of pin 180 contacts the still-plastic polymer and compresses it, causing the polymer to flow outward from the limited volume between flat face 192 and bottom wall 188. The compressed material between flat face 192 and bottom wall 188 forms platform 130 of bottle 102. The displaced material flows outward from the platform and forms rim 132 surrounding platform 130. Thus the extension of pin 180 a predetermined distance 194 from bottom wall 188 while the polymer is still plastic forms the desired structure of the anchor region. The distance between flat face 192 and bottom wall 188 (and polymer shrinkage properties) determines the thickness of the base in the platform. The amount of polymer adjacent bottom wall 188 after expansion determines the height of rim 132. This amount is in turn determined by the geometries of parison 182, pin 180, and cavity 186 and by the blow molding process parameters. In some embodiments, pin 180 includes one or more holes in its sides to supply pressurized air for the expansion phase of the process.

Once the polymer used to form the bottle has cooled sufficiently, pin 180 can be withdrawn. Then, opening of the mold allows removal of a fully formed bottle. A pipe may then be inserted through the bottle opening in the appropriate orientation and the endplate attached to the platform.

The embodiment of the process described above includes a pin having a flat face disposed perpendicular to the pin's axis producing a useful platform and rim. However, the described process may be more generally applicable whenever defined geometry with tight tolerances is required on the interior of a blow molded part. In other embodiments, the pin may include a face that is not flat or not perpendicular to the pin's axis. The pin may include any of a variety of structures on its end to produce complementary geometry on the inside bottom of the bottle. Useful geometry may include, without limitation, welding energy directors, snap features, grooves for adhesive or seals, or controlled-size recesses or holes.

As illustrated in FIG. 14, steps of an embodiment of the process 1400 include extruding a parison 1402; expanding the parison into a mold 1404; extending a pin 1406; and compressing a portion of the bottle 1408. As described above, the pin has a formed face and extends through the inlet of the parison. The mold has a wall opposed to the inlet so that extending the pin a predetermined distance from the wall forces plastic material of the parison outward thereby forming a platform surrounded by a raised rim. The thickness of the bottle in the platform area is set by the predetermined distance, with an allowance for material shrinkage. The distance between the pin face and the wall also determines the size of the raised rim by displacing "excess" material out of the platform area to form the rim. The finished bottle is ejected from the mold at step 1410. The step of forming the pipe 1412 is independent of the above steps. Assembly of the completed reagent container includes steps of inserting the pipe through the bottle opening 1414; engaging the top end of the pipe with the bottle opening 1416; and attaching the endplate to the platform 1418.

The embodiment of the process described above is based upon extrusion blow molding. Other embodiments may use variations of injection blow molding where an injection molded preform replaces the extruded parison. In either embodiment, the shape of the platform and rim is defined by the positioning of the face of the pin to compress and displace the still-plastic polymer, causing the polymer to flow outward from the limited volume between the pin face and the bottom wall of the mold.

The above description includes embodiments described as having features, structure, or characteristics. These references indicate that the embodiments described can include a particular feature, but every embodiment does not necessarily include every described feature, structure, or characteristic. Further, the description of a particular feature, structure, or characteristic in connection with a particular embodiment is exemplary only; it should be understood that it is within the knowledge of one skilled in the art to include such feature, structure, or characteristic in connection with other embodiments whether or not explicitly described.

Unless otherwise indicated, all numbers used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the claims. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventors expect skilled artisans to employ such variations as appropriate, and the inventors intend for the invention to be practiced otherwise than specifically described herein. Accordingly, this specification and claims include all modifications and equivalents of the subject matter recited in the claims appended hereto as permitted by applicable law. Moreover, any combination of the above-described elements in all possible variations thereof is encompassed by the specification and claims unless otherwise indicated herein or otherwise clearly contradicted by context.

In closing, it is to be understood that the embodiments disclosed herein are illustrative of the principles of the present invention. Other modifications that may be employed are within the scope of the invention. Thus, by way of example, but not of limitation, alternative configurations may be utilized in accordance with the teachings herein. Accordingly, the present invention is not limited to that precisely as shown and described.

We claim:

1. A reagent container comprising:
    an elongated blow-molded bottle including a bottom wall, a top wall, a side wall, an inner wall and an end wall, the top wall having an opening and opposed to the bottom wall, the inner wall shorter than the end wall, the side wall and the end wall connecting the bottom wall to the top wall; and
    a pipe including an open top end, a bottom end, and a tube wall extending from the top end to the bottom end, the tube wall having an aperture adjacent the bottom end, and the bottom end including an endplate covering less than about half of the bottom end,
    wherein the pipe is disposed in and affixed to the bottle with the top end positioned within the bottle opening, and the aperture disposed toward the end wall.

2. The reagent container of claim 1 wherein the bottom wall has a controlled surface surrounded by a raised rim, the controlled surface disposed inside the bottle and opposite the opening, and wherein the pipe is affixed to the bottle by attaching the endplate to the controlled surface.

3. The reagent container of claim 2, wherein the controlled surface is flat to within about 0.2 mm and wherein the endplate is ultrasonically welded to the controlled surface.

4. The reagent container of claim 2, wherein the raised rim extends about 1 to 3 mm above the controlled surface.

5. The reagent container of claim 2, wherein the bottle includes a parting line and the controlled surface overlays the parting line.

6. The reagent container of claim 1, wherein the tube wall has one or more ribs extending outwardly from the tube wall, and wherein the pipe is affixed to the bottle by an interference fit between the plurality of ribs and the opening.

7. The reagent container of claim 6 wherein the tube wall, at least one of ribs, and the opening define a vent passage outside of the pipe.

8. The reagent container of claim 6, wherein the bottle is substantially wedge-shaped and the side wall includes a first converging wall, a second converging wall, and an end wall connecting the first converging wall to the second converging wall, and wherein the tube wall has a first straight segment and a second straight segment, wherein the first straight segment is disposed substantially parallel to the first converging wall and the second straight segment is disposed substantially parallel to the second converging wall.

9. The reagent container of claim 8, wherein the pipe has a diameter between about one-fifth and about one-third of the distance between the first converging wall and the second converging wall measured at the opening.

10. A reagent container comprising:
    a bottle including a top wall, a first side wall, and a second side wall, the top wall having an opening, and the first side wall and the second side wall connected to the top wall; and
    a pipe disposed in the bottle opening, the pipe including a central axis, a top end, a bottom end, and a tube wall disposed about the central axis and connecting the top end to the bottom end, the tube wall having first and second straight segments extending parallel to the central axis, and the bottom end including an endplate covering less than about half of the bottom end,
    wherein the first straight segment is disposed substantially parallel to the first side wall and the second straight segment is disposed substantially parallel to the second side wall.

11. The reagent container of claim 10, wherein the tube wall surrounds and defines a lumen, wherein the pipe further includes one or more ribs extending outwardly from the tube wall, wherein the top end is disposed in the opening, and wherein the tube wall, at least one of the one or more ribs, and the opening define a vent passage outside of the lumen.

12. The reagent container of claim 11 wherein the bottle further includes an end wall connected between the first side wall and the second side wall, the end wall shorter than the first side wall and shorter than the second side wall, and wherein the pipe further includes an aperture in the tube wall, the aperture oriented towards the end wall.

13. The reagent container of claim 12 wherein the bottle further includes a bottom wall disposed substantially parallel to the top wall, the bottom wall connecting the first side wall, to the second side wall, and to the end wall, the bottom wall having a circular platform surrounded by a raised rim, wherein the platform is opposed to the opening, and wherein the endplate is attached to the platform.

14. The reagent container of claim 13 wherein the tube wall further includes an arcuate segment between the first straight segment and the second straight segment and wherein at least one of the plurality of ribs extend outwardly from the arcuate segment.

* * * * *